US008088964B2

(12) United States Patent
Mouton

(10) Patent No.: US 8,088,964 B2
(45) Date of Patent: Jan. 3, 2012

(54) WOUND DRESSING

(75) Inventor: Jacobus Frederick Mouton, Centurion (ZA)

(73) Assignee: IWMT Intellectual Property Holdings (Proprietary) Limited (ZA)

( * ) Notice: Subject to any disclaimer, the term of this patent is extended or adjusted under 35 U.S.C. 154(b) by 565 days.

(21) Appl. No.: 12/162,110

(22) PCT Filed: Mar. 31, 2006

(86) PCT No.: PCT/IB2006/000751
§ 371 (c)(1),
(2), (4) Date: Jan. 12, 2009

(87) PCT Pub. No.: WO2007/085884
PCT Pub. Date: Aug. 2, 2007

(65) Prior Publication Data
US 2009/0221946 A1    Sep. 3, 2009

(30) Foreign Application Priority Data
Jan. 24, 2006 (ZA) .................................. 2006/00686

(51) Int. Cl.
*A61F 15/00* (2006.01)
(52) U.S. Cl. ................ 602/43; 602/41; 602/42
(58) Field of Classification Search .............. 602/41–59; 604/383
See application file for complete search history.

(56) References Cited

U.S. PATENT DOCUMENTS

| 5,437,621 | A | * | 8/1995 | Andrews et al. | 602/42 |
| 5,632,731 | A | * | 5/1997 | Patel | 602/59 |
| 5,879,487 | A | | 3/1999 | Ravella et al. | |
| 6,077,526 | A | * | 6/2000 | Scully et al. | 424/443 |
| 6,653,520 | B1 | * | 11/2003 | Mouton | 602/45 |
| 2006/0020234 | A1 | * | 1/2006 | Chou et al. | 602/41 |

FOREIGN PATENT DOCUMENTS

| EP | 0849388 A1 * | 6/1998 |
| WO | WO 0018343 A1 * | 4/2000 |
| WO | 01/34079 | 5/2001 |

OTHER PUBLICATIONS

Written Opinion of the International Searching Authority issued in related International Patent Application No. PCT/IB2006/000751.
International Search Report from related PCT application, dated Apr. 9, 2006.

* cited by examiner

*Primary Examiner* — Kim M Lewis
(74) *Attorney, Agent, or Firm* — Grossman Tucker Perreault & Pfleger PLLC

(57) ABSTRACT

This invention relates to a wound dressing (10). The wound dressing includes first and second absorbent layers (12, 14) of a non-woven fabric of viscose and polyester fibres. Each absorbent layer has an operatively inner face (20, 26) and an operatively outer face (18, 22). The first and the second absorbent layers are bonded together with their operatively inner faces in face-to-face relationship, such that the absorbent layers together form a pad. The bonding between the first and second absorbent layers may be effected by a needle-punching process in which the needle punching density is no more than 400 punches/cm2. The wound dressing further includes a third layer (16) sandwiched between and bonded to the first and second absorbent layers. The third layer is in the form of cotton gauze. The invention extends to a method of making a wound dressing, and to a method of treating a wound.

31 Claims, 2 Drawing Sheets

WOUND DRESSING

CROSS-REFERENCE TO RELATED APPLICATIONS

This application is the U.S. National Stage of International PCT Application No. PCT/IB2006/00751 filed on Mar. 31, 2006, which claims priority to South African Application No. 2006/00686 filed Jan. 24, 2006, both of which are fully incorporated herein by reference.

This invention relates to a wound dressing. It relates also to a method of making a wound dressing, and to a method of treating a wound.

In accordance with one aspect of the invention there is provided a wound dressing which includes first and second absorbent layers, the first and second absorbent layers each being of a non-woven fabric of viscose and polyester fibres, each absorbent layer having an operatively inner face and an operatively outer face, the first and the second absorbent layers being bonded together with their operatively inner faces in face-to-face relationship, and a third layer of cotton fibres sandwiched between and bonded to the first and the second absorbent layers, such that the two absorbent layers and the third layer together form a three-layered laminate pad, the bonding between the first, second and third layers being effected by means of a needle-punching process in which the needle punching density is no more than 400 punches/cm$^2$.

Both the first and the second absorbent layers may be in the form of needle punched fibre batts or mats.

The first and second absorbent layers may each comprise 60-80% viscose fibres by volume and 20-40% polyester fibres by volume. More particularly, the first and second absorbent layers may each comprise about 70% viscose fibres by volume and about 30% polyester fibres by volume.

The needle punching density of the needle-punching process may be 300-350 punches/cm$^2$ (i.e. 3000000-3500000 punches/m$^2$).

The viscose and polyester fibres of the first and the second absorbent layers may have a fineness of 2-2.5 denier. The viscose and the polyester fibres of the first and the second absorbent layers may have a length of 4.5-5.5 cm, e.g. about 5 cm (i.e. about 0.05 m). The viscose fibres and the polyester fibres may be porous fibres.

Each of the first and the second absorbent layers may have a weight per unit area of 280-320 g/m$^2$, e.g. 300 g/m$^2$ (i.e. 0.3 kg/m$^2$).

The third layer may be made of said cotton fibres or of cotton threads. The third layer will thus also be absorbent. The third layer may be in the form of cotton gauze. The fibre or thread density of the third layer may be in the order of 45-50 threads/cm$^2$, e.g. 47 threads/cm$^2$. The third layer may have a yarn count of 35-45, e.g. 40. The third layer may have a weight per unit area of 55-65 g/m$^2$, e.g. 60 g/m$^2$ (i.e. 0.06 kg/m$^2$).

The wound dressing may have a weight per unit area of 615-705 g/m$^2$, e.g. 660 g/m$^2$. The wound dressing may have a thickness of no more than 3.5 mm, e.g. it may have a thickness of about 2.8-3 mm (i.e. about 0.028-0.03 m).

The operatively outer face of at least one of the first and the second absorbent layers may have been subjected to a thermal treatment process, to provide said operatively outer face with a substantially smooth surface. The operatively outer faces of both the first and the second absorbent layers may have been subjected to the thermal treatment process, so that both said operatively outer faces and, accordingly, outer faces of the dressing have said substantially smooth surfaces. The wound dressing can thus be used with either one of its operatively outer faces facing towards or in contact with a wound.

In accordance with another aspect of the invention there is provided a method of making a wound dressing, which method includes:

manufacturing two needle-punched fibre batts of viscose and polyester fibres by means of a needleloom, each batt having an operatively inner face and an operatively outer face;

locating the two fibre batts with their operatively inner faces in face-to-face relationship;

sandwiching a layer of cotton gauze between the two fibre batts; and bonding the two fibre batts and the layer of cotton gauze sandwiched therebetween together by a needle-punching process in which the needle punching density is no more than 400 needle punches/cm$^2$, such that the two fibre batts together form a three-layered laminate pad.

Each of the two fibre batts may be manufactured of 60-80% viscose fibres and 20-40% polyester fibres. In particular, each of the two fibre batts may be manufactured of about 70% viscose fibres and about 30% polyester fibres.

The needle punching density of the needle-punching process bonding the two fibre batts together may be 300-350 punches/cm$^2$.

The fibres from which the two fibre batts are manufactured may have a fineness of 2-2.5 denier. The fibres from which the two fibre batts are manufactured may have a length of 4.5-5.5 cm, e.g. about 5 cm. The viscose fibres and the polyester fibres from which the two fibre batts are manufactured may be porous fibres. Each of the two fibre batts may be manufactured to have a weight per unit area of 280-320 g/m$^2$, e.g. about 300 g/m$^2$.

The layer of cotton gauze may be made of cotton fibres or threads, the fibre or thread density of the layer being in the order of 45-50 threads/cm$^2$, e.g. 47 threads/cm$^2$. The layer of cotton gauze may have a yarn count of 35-45, e.g. 40. The layer of cotton gauze may have a weight per unit area of 55-65 g/m$^2$, e.g. 60 g/m$^2$.

The three-layered laminate pad may be manufactured to have a weight per unit area of 615-705 g/m$^2$, e.g. 660 g/m$^2$.

The laminate pad may be manufactured to have a thickness of no more than 3.5 mm, e.g. it may be manufactured to have a thickness of about 2.8-3 mm.

The method may also include heat treating the operatively outer face of at least one of the two fibre batts, to provide said operatively outer face with a substantially smooth surface. Advantageously, the method may include heat treating the operatively outer faces of both fibre batts, such that both said operatively outer faces and, accordingly, outer faces of the laminate pad have said substantially smooth surfaces.

In accordance with a further aspect of the invention there is provided a method of treating a wound, which method includes dressing the wound by making use of a wound dressing as hereinbefore described.

In accordance with a yet further aspect of the invention there is provided a method of treating a wound, which method includes dressing the wound by making use of a wound dressing made in accordance with a method as hereinbefore described.

The invention is now described, by way of a non-limiting example, with reference to the accompanying diagrammatic drawings.

Figure 1:
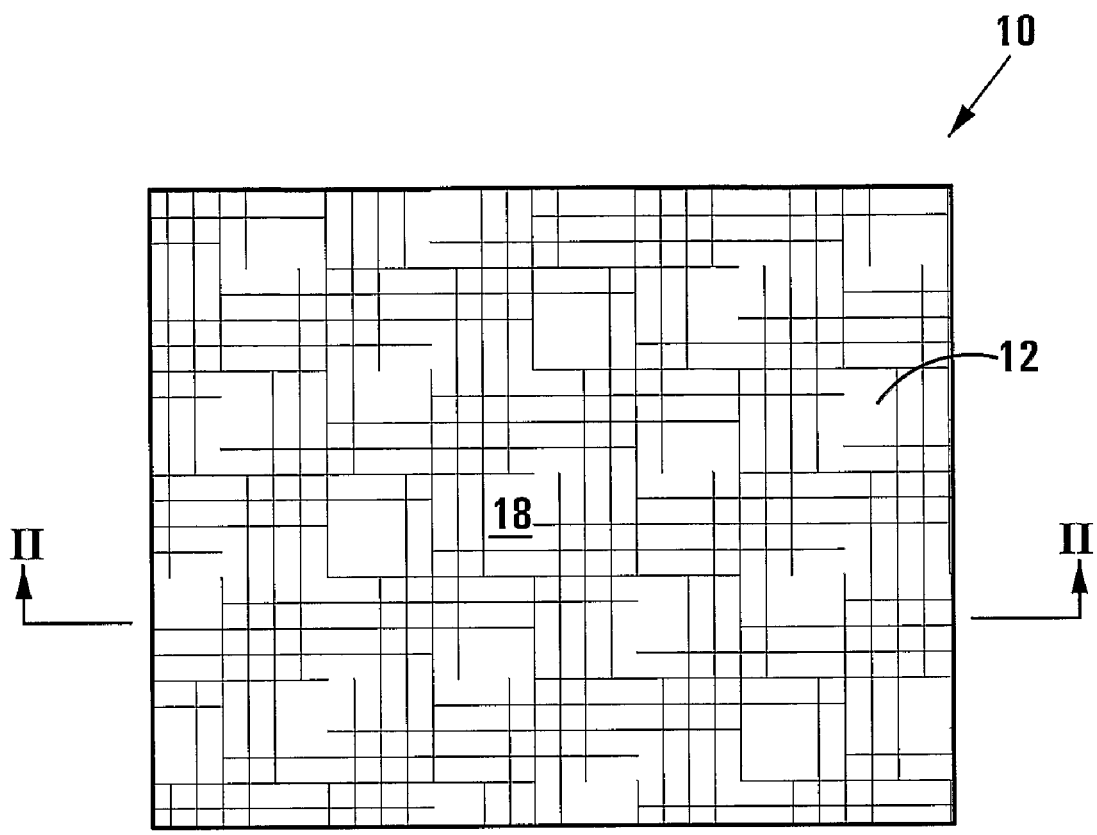
FIG. 1 shows, schematically, a face-on elevation of a wound dressing in accordance with the invention.
Figure 2:
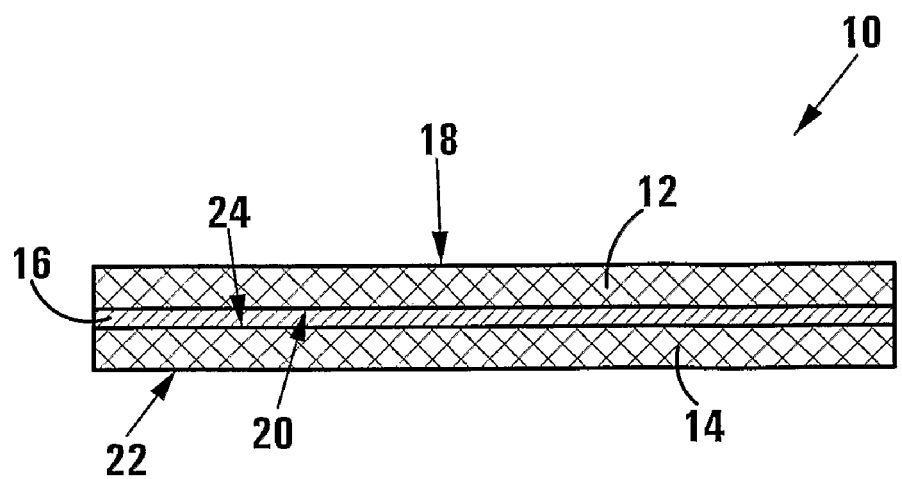
FIG. 2 shows, schematically, a cross-sectional elevation of the wound dressing in accordance with the invention taken at II-II in FIG. 1.

With reference to FIGS. 1 and 2 of the drawings, a wound dressing in accordance with the invention is generally designated by reference numeral 10. For clarity, the thickness of the wound dressing 10 is exaggerated in FIG. 2. The wound dressing 10 is in the form of a rectangular laminate pad which comprises first and second absorbent layers 12, 14 and a third layer 16 sandwiched between and bonded to the first and second absorbent layers 12, 14. The three layers 12, 14, 16 are bonded together by means of a needle-punching process as hereinafter described in further detail.

Each of the first and second absorbent layers 12, 14 is of a non-woven fabric comprising about 70% viscose fibres by volume and about 30% polyester fibres by volume. The viscose fibres and polyester fibres are porous fibres having a length of about 5.08 cm (2 inches) and a fineness of 2-2.5 denier. Further, each of the first and second absorbent layers 12, 14 have a weight per unit area of about 300 g/m$^2$.

The third layer 16 is in the form of cotton gauze made of 100% cotton fibres or threads, and the fibre or thread density of the third layer 16 is about 47 threads/cm$^2$. The third layer 16 has a yarn count of 40, and has a weight per unit area of about 60 g/m$^2$.

The wound dressing 10 thus has a total weight per unit area of about 660 g/m$^2$, and has a total thickness of about 2.8-3 mm.

In particular, each of the first and second absorbent layers 12, 14 is in the form of a fibre batt or mat. The first absorbent layer 12 has an operatively outer face 18 and an operatively inner face 20, and the second absorbent layer 14 has an operatively outer face 22 and an operatively inner face 24. The first and second absorbent layers 12, 14 are oriented such that their operatively inner faces 20, 24 are in face-to-face relationship, with the third layer 16 thus being in contact with the operatively inner faces 20, 24 of the first and second absorbent layers 12, 14. The three layers 12, 14, 16 together form a three-layered laminate pad or body.

As mentioned above, the first and second absorbent layers 12, 14 and the third layer 16 are bonded together by means of a needle-punching process, the needle punching density of the needle-punching process effecting such bonding together of the layers 12, 14, 16 being about 300-350 punches/cm$^2$. Further, the operatively outer layers 18, 22 of the first and second absorbent layers 12, 14 have been subjected to heat treatment, such that the wound dressing 10 is provided with substantially smooth and non-adherent outer faces, as will become more apparent hereinafter when manufacturing of the wound dressing 10 is described in more detail.

In another embodiment (not shown), the third layer 16 can be omitted, in which case the first and second absorbent layers 12, 14 are bonded together such that their operatively inner faces 20, 24 are in contact with each other.

Figure 3:
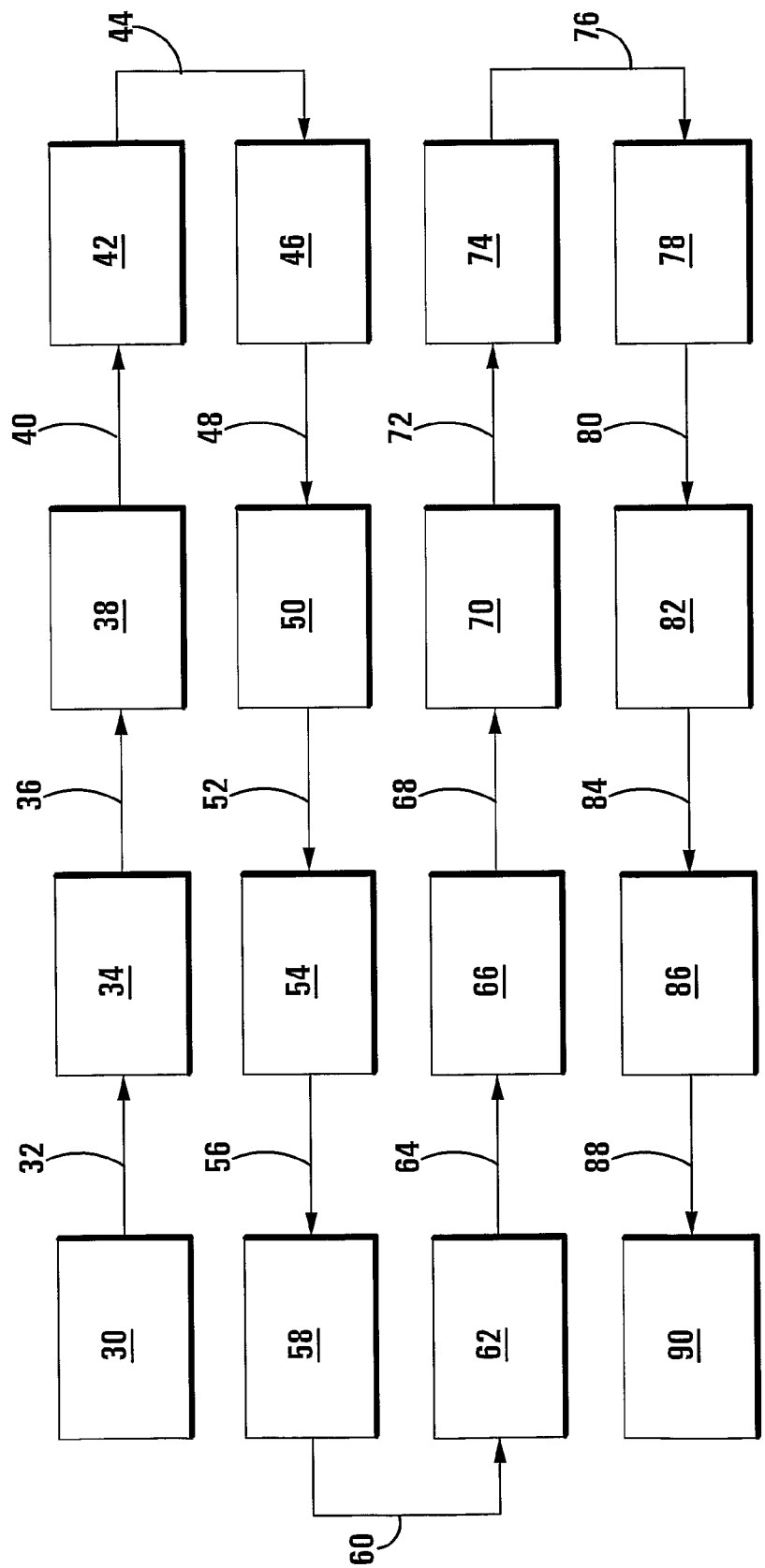
FIG. 3 shows, schematically, a flow-diagram of steps forming part of the method of making a wound dressing in accordance with the invention.

FIG. 3 shows a flow diagram of steps employed in a method of making a wound dressing in accordance with the invention. In this figure, block 30 represents a blending process during which the 70% viscose fibres and 30% polyester fibres from which each of the absorbent layers 12, 14 are manufactured, are blended. The blended fibres are then moved along a notional flow line 32 to a size-reduction process represented by block 34, during which size-reduction process the size of blended fibre tufts are reduced. After the size reduction, the fibre tufts are moved along a notional flow line 36 to a carding process, represented by block 38, during which carding process the fibres are combed and disentangled, to arrange them in to a fibrous web having more or less parallel fibres. After carding, the fibrous web is moved along a notional flow line 40 to a cross-lapping process, represented by block 42. During the cross-lapping process, the fibrous web is build up, by layering, to the desired finished non-woven weight. After cross-lapping, the fibrous web is moved along a notional flow line 44 to a needleloom where needle-punching takes place, to bond the fibres of the web together.

In this example, the fibrous web from which each of the absorbent layers 12, 14 is formed undergoes four needle-punching runs, the various needle-punching runs being notionally represented by blocks 46, 50, 54 and 58. Thus, the fibrous web passes through four needle boards. In this example, the needleloom employed to effect the needle-punching is a felting loom having four needle boards, so that the fibrous web is fed through the needleloom once only. Flow lines 48, 52 and 56 notionally represent movement of the fibrous web respectively from the needle-punching run 46 to the needle-punching run 50, from the needle-punching run 50 to the needle-punching run 54, and from the needle-punching run 54 to the needle-punching run 58.

Each of the needle boards of the needle loom is 0.25 m wide and 1 m long, and has 4,000 needles mounted thereon. Thus, each needle board has 16,000 needles/linear meter. Each of the needles has a diameter of 0.58 mm, has a taper- or conical point and has 9 barbs. The fibrous web is fed through the needleloom at a feed rate of 3 m/minute, and the punching frequency of each needle board is 800-1,000 punches/minute. A punching density of between 300 and 427 punches/cm$^2$, depending on the punching frequency, is thus obtained during each of the needle-punching runs 46, 50, 54, 58. The fibrous web exposed to the needle-punching runs 46, 50, 54, 58 thus yields a fibrous batt or mat which has been exposed to a total needle-punching density of between about 1,200 and 1,707 punches/cm$^2$.

During the first needle-punching run 46, the depth to which the needles penetrate the fibrous web is about 5.4 mm, during the second needle-punching run 50 the depth of needle penetration is about 4.6 mm, during the third needle-punching run 54 the depth of needle penetration is about 4.3 mm, and during the fourth and final needle-punching run 58 the depth of needle penetration is about 3.2 mm.

As mentioned above, once the fibrous web has been exposed to the aforedescribed needle-punching process, a fibrous batt or mat is formed. Said fibrous batt is then, if required, moved along a notional flow line 60 to a chemical treatment process, represented by block 62, where the fibrous batt can be chemically treated. After said chemical treatment of the batt, one major face of the fibrous batt, which face is intended to form one of the operatively outer faces 18, 22 of the first and second absorbent layers 12, 14, is then exposed to a heat treatment process to provide said outer face of the fibrous mat with a smooth, relatively non-fluffed and non-adherent surface. Movement of the fibrous web from the chemical treatment process 62 to the heat treatment process is indicated by notional flow line 64, the heat treatment process being represented by block 66. If chemical treatment of the fibrous batt is not required, as is the case with the present example, it is moved directly from the needle-punching run 58 to the heat treatment process 66. Subsequent to the aforedescribed heat treatment, the fibrous batt is then moved along a notional flow line 68 to a winding and cutting process, represented by block 70, where the batt is cut into the required width and is wound onto a roller.

The third or cotton gauze layer 16 is manufactured by means of a conventional gauze manufacturing process and, accordingly, manufacturing thereof is not described.

Referring back to the flow diagram of FIG. 3, a notional flow line 72 represents movement of two rolls of manufactured fibrous batt to a layering process, represented by block 74, where the layer of cotton gauze 16 is sandwiched between the first and second absorbent layers 12, 14, each of which is in the form of the aforedescribed fibrous batt. In particular, the fibrous batts or absorbent layers 12, 14 are oriented such that their smoothened faces or surfaces, i.e. those faces or surfaces which underwent heat treatment, face operatively outwardly. After sandwiching of the three layers 12, 14, 16, the layers are moved along a notional flow line 76 to a needleloom which effects a bonding needle-punching process or run, represented by block 78. The needleloom used for the bonding needle-punching process or run 78 is a loom having a single needle board. The three layers are thus bonded together by means of the needle-punching run represented by block 78. During this bonding needle-punching run 78, the feed rate, the type of and number of needles mounted on the needle board and the dimensions of the needle board used is the same as that used during the needle-punching runs 46, 50, 54, 58. During the bonding needle-punching run 78, the punching frequency of the needle board is such that a bonding punching density of about 300-350 punches/cm$^2$ is obtained. After the bonding needle-punching run 78, a sheet, which is in the form of a three-layered laminate pad, is thus yielded. The laminate pad or sheet is then moved along a notional flow line 80 to a cutting process, indicated by block 82, where it is cut to yield the required size wound dressings 10. After the wound dressings 10 have been cut to the required size, they are moved along a notional flow line 84 to a packing station 86, where they are packaged, typically separately packaged into airtight packages. The packaged wound dressings are then moved along a notional flow line 88 to a sterilization process, represented by a block 90, where the packaged wound dressings are sterilized in conventional fashion.

Naturally, the aforedescribed steps for making a wound dressing in accordance with the invention need not all be executed on the same production line. In fact, all the steps need not even be executed at the same location or manufacturing plant.

Although the method, as far as manufacturing of the first and second absorbent layers 12, 14 are concerned, is hereinbefore described with reference to a needleloom which includes four needle boards, it is to be appreciated that a needle loom having a single needle board can also advantageously be applied, in which case the fibrous web will be fed four times through the needle loom.

By employing the method and raw materials as hereinbefore described, a wound dressing having a thickness of about 2.8-3 mm is obtained.

The invention as described and illustrated provides a wound dressing which can be used to dress a wide spectrum of wounds including, inter alia, burn wounds, infection wounds, surgical wounds, diabetic foot wounds, external cancer wounds, fungating wounds, wounds associated with HIV, pressure sores, leg ulcers, leprosy wounds, amputation wounds, chronic wounds, and superficial wounds in both humans and animals. Use of the wound dressing in accordance with the invention is not limited to surface wounds, but can also be inserted into deep wounds or cuts. Further, the wound dressing in accordance with the invention can be cut into any desired size or shape, without affecting the properties thereof.

The porous viscose fibres have high moisture absorbing properties and are air-permeable. In turn, polyester fibres are relatively tough and strong and have high abrasion resistance. In addition, polyester fibres have the ability after heat treatment, to retain a smoothened or flattened profile. Because of the combination of viscose and polyester fibres of the absorbent layers 12, 14 of the present wound dressing, each of the outer layers 12, 14, whilst being air-permeable, has exceptional moisture absorbing properties, thus yielding a relatively tough and strong wound dressing with high moisture absorbing properties. Further, because of the softness of porous viscose fibres, the wound dressing 10 is relatively soft and thus resists discomfort to a patient whose wound is dressed by a wound dressing in accordance with the invention.

The wound dressing in accordance with the invention, by virtue of its particular construction and the way in which it is manufactured, has the ability not only to absorb exudate from wounds, but also, because of capillary action stemming from the construction of the dressing, to direct absorbed exudates and bacteria away from a wound. Further, the wound dressing in accordance with the invention, because of said capillary action, has the ability to "kick-start" wounds that are classified as unresponsive or dead wounds, i.e. wounds which do not exude moist or liquids. Furthermore, the wound dressing has the ability to retain absorbed exudate, such that absorbed moist does not leak or drip therefrom.

Furthermore, because both the outer surfaces of the wound dressing 10 are smoothened by the aforedescribed heat treatment process, the dressing is non-directional, i.e. it can be used with either of its faces in contact with a wound. Because the outer surfaces of the wound dressing are relatively non-adherent, the dressing in accordance with the invention can comfortably be used with ointment employed in treatment of wounds.

Two or more wound dressings in accordance with the invention can be stacked one on top of the other, or they can be placed in contact with each other or one another such that they overlap, with only one, or more, of them in direct contact with a wound to be treated. In a case where a number of dressings are simultaneously used, but only one of them is in direct contact with a wound, exudate and bacteria will, by virtue of the capillary action, migrate from the wound dressing in direct contact with the wound to the other wound dressing or wound dressings in contact, either directly or via an intermediate dressing or dressings, with said one wound dressing in direct contact with the wound.

The invention as described and illustrated thus provides a wound dressing which not only has good absorption qualities, but also serves to direct absorbed exudates, including bacteria, away from a wound being treated, which, as will be appreciated, speeds up the healing of the wound.

What is claimed is:

1. A wound dressing which includes first and second absorbent layers, the first and second absorbent layers each being of a non-woven fabric of viscose and polyester fibres, each absorbent layer having an operatively inner face and an operatively outer face, the first and the second absorbent layers being bonded together with their operatively inner faces in face-to-face relationship, and a third layer of cotton fibres sandwiched between and bonded to the first and the second absorbent layers, such that the two absorbent layers and the third layer together form a three-layered laminate pad, the bonding between the first, second and third layers being effected by means of a needle-punching process in which the needle punching density is no more than 400 punches/cm$^2$.

2. A wound dressing as claimed in claim 1, in which the first and second absorbent layers each comprises 60-80% viscose fibres and 20-40% polyester fibres.

3. A wound dressing as claimed in claim 2, in which the first and second absorbent layers each comprises about 70% viscose fibres and about 30% polyester fibres.

4. A wound dressing as claimed in claim 1, in which the needle punching density of the needle-punching process is 300-350 punches/cm$^2$.

5. A wound dressing as claimed in claim 1, in which the viscose and polyester fibres of the first and the second absorbent layers have a fineness of 2-2.5 denier.

6. A wound dressing as claimed in claim 1, in which the viscose and the polyester fibres of the first and the second absorbent layers have a length of 4.5-5.5 cm.

7. A wound dressing as claimed in claim 1, in which the viscose fibres and the polyester fibres are porous fibres.

8. A wound dressing as claimed in claim 1, in which each of the first and the second absorbent layers have a weight per unit area of 280-320 g/m$^2$.

9. A wound dressing as claimed in claim 1, in which the third layer is in the form of cotton gauze.

10. A wound dressing as claimed in claim 9, in which the fibre or thread density of the third layer is in the order of 45-50 threads/cm$^2$.

11. A wound dressing as claimed in claim 1 or claim 9, in which the third layer has a yarn count of 35-45.

12. A wound dressing as claimed in claim 1, in which the third layer has a weight per unit area of 55-65 g/m$^2$.

13. A wound dressing as claimed in claim 1, which has a weight per unit area of 615-705 g/m$^2$.

14. A wound dressing as claimed in claim 1, which has a thickness of no more than 3.5 mm.

15. A wound dressing as claimed in claim 1, in which the operatively outer face of at least one of the first and the second absorbent layers has been subjected to a thermal treatment process, to provide said operatively outer face with a substantially smooth surface.

16. A wound dressing as claimed in claim 15, in which the operatively outer faces of both the first and the second absorbent layers have been subjected to the thermal treatment process, so that both said operatively outer faces and, accordingly, outer faces of the dressing have said substantially smooth surfaces.

17. A method of making a wound dressing, which method includes:
   manufacturing two needle-punched fibre batts of viscose and polyester fibres by means of a needleloom, each batt having an operatively inner face and an operatively outer face;
   locating the two fibre batts with their operatively inner faces in face-to-face relationship;
   sandwiching a layer of cotton gauze between the two fibre batts; and
   bonding the two fibre batts and the layer of cotton gauze sandwiched therebetween together by a needle-punching process in which the needle punching density is no more than 400 needle punches/cm$^2$, such that the two fibre batts and the layer of cotton gauze form a three-layered laminate pad.

18. A method as claimed in claim 17, in which each of the two fibre batts is manufactured of 60-80% viscose fibres and 20-40% polyester fibres.

19. A method as claimed in claim 18, in which each of the two fibre batts is manufactured of about 70% viscose fibres and about 30% polyester fibres.

20. A method as claimed in claim 17, in which the needle punching density of the needle-punching process bonding the two fibre batts together is 300-350 punches/cm$^2$.

21. A method as claimed in claim 17, in which the fibres from which the two fibre batts are manufactured have a fineness of 2-2.5 denier.

22. A method as claimed in claim 17, in which the fibres from which the two fibre batts are manufactured have a length of 4.5-5.5 cm.

23. A method as claimed in claim 17, in which the viscose fibres and the polyester fibres from which the two fibre batts are manufactured are porous fibres.

24. A method as claimed claim 17, in which each of the two fibre batts are manufactured to have a weight per unit area of 280-320 g/m$^2$.

25. A method as claimed in claim 17, in which the layer of cotton gauze is made of cotton fibres or threads, the fibre or thread density of the layer being in the order of 45-50 threads/cm$^2$.

26. A method as claimed in claim 17, in which the layer of cotton gauze has a yarn count of 35-45.

27. A method as claimed in claim 17, in which the layer of cotton gauze has a weight per unit area of 55-65 g/m$^2$.

28. A method as claimed in claim 27, in which the three-layered laminate pad is manufactured to have a weight per unit area of 615-705 g/m$^2$.

29. A method as claimed in claim 17, in which the laminate pad is manufactured to have a thickness of no more than 3.5 mm.

30. A method as claimed in claim 17, which includes heat treating the operatively outer face of at least one of the two fibre batts, to provide said operatively outer face with a substantially smooth surface.

31. A method as claimed in claim 30, which includes heat treating the operatively outer faces of both fibre batts, such that both said operatively outer faces and, accordingly, outer faces of the laminate pad have said substantially smooth surfaces.

* * * * *